(12) United States Patent
Schley

(10) Patent No.: US 6,490,908 B2
(45) Date of Patent: Dec. 10, 2002

(54) METHOD AND DEVICE FOR DETERMINING THE GAS PROPERTIES OF A COMBUSTIBLE GAS

(75) Inventor: Peter Schley, Essen (DE)

(73) Assignee: Buhrgas Aktiengesellschaft (DE)

( * ) Notice: Subject to any disclaimer, the term of this patent is extended or adjusted under 35 U.S.C. 154(b) by 0 days.

(21) Appl. No.: 09/967,584

(22) Filed: Sep. 28, 2001

(65) Prior Publication Data

US 2002/0040590 A1 Apr. 11, 2002

(30) Foreign Application Priority Data

Sep. 29, 2000 (DE) ......................................... 100 48 839
May 3, 2001 (DE) ......................................... 101 21 641

(51) Int. Cl.[7] ........................ G01N 19/10; G01N 25/22; G01J 3/30

(52) U.S. Cl. ........................ 73/23.2; 356/311; 374/36

(58) Field of Search .............................. 73/23.2, 25.01; 44/301; 250/339.13; 356/311, 303, 437; 374/36, 37

(56) References Cited

U.S. PATENT DOCUMENTS 3,836,255 A * 9/1974 Schuman ................... 356/311

* cited by examiner

Primary Examiner—Hezron Williams
Assistant Examiner—Jay Politzer
(74) Attorney, Agent, or Firm—Blakely Sokoloff Taylor & Zafman

(57) ABSTRACT

The invention relates to a method and a device to determine the gas properties of combustible gas, in particular of natural gas, wherein a) at least part of the combustible gas is exposed to infrared radiation and the amount of infrared radiation absorbed by the combustible gas is determined for two wave lengths or spectral ranges, the two wave lengths or spectral ranges being selected so that the amounts of individual components of the combustible gas in their different percentages have an effect on the amounts absorbed and recorded, b) the thermal conductivity is recorded and c) the gas properties are determined from the three measurands.

The term gas properties is understood to mean the gas composition, the gross heating value, the Wobbe number, the normal density and the methane number.

10 Claims, 6 Drawing Sheets

METHOD AND DEVICE FOR DETERMINING THE GAS PROPERTIES OF A COMBUSTIBLE GAS

BACKGROUND IF THE INVENTION

1. Field of the Invention

The invention relates to a method and a device for determining the gas properties of a combustible gas. The term gas properties is understood to mean the gas composition, the gross heating value, the Wobbe number or Wobbe index, the normal density and the methane number.

2. Description of the Prior Art

The gross heating value can be the molar, mass-based or volume-based gross heating value. The gross heating value of natural gas must be measured when the gas is handed over from the supplier to the customer so that it can be billed. For example, in practice calorimeters or gas chromatographs are used to determine the gross heating value at delivery stations where gas changes hands between two gas supply companies. When gas chromatographs are used, the gas composition is analysed. Once the gas composition has been established, the gross heating value of the combustible gas can be determined on the basis of the gross heating value for the pure substances. When gas meters, particularly turbine meters, are used, the volume flow rate is measured. The volume flow rate must be converted with the aid of the compressibility number from the operating condition to the normal condition. The compressibility number can be calculated with the known SGERG method (ISO 12213) from the gross heating value, normal density and amount of $CO_2$. If the gross heating value is determined using a calorimeter, the normal density and the amount of $CO_2$ must also be measured. If a gas chromatograph is used, the normal density and amount of $CO_2$ can be calculated from the gas composition. The amount of energy is determined as the product of the gross heating value and the standard volume flow rate.

The methods for determining the gross heating value which use calorimeters or gas chromatographs provide very good results but the technology is complicated and this means very high investment and maintenance costs. Such methods are too complicated and have too slow a response time for some industrial applications, in particular for control and regulating purposes.

Correlative methods are also used to determine the gross heating value or the amount of energy when gas transported under high pressure is to be billed. These correlative methods measure several physical or chemical variables and then calculate the gross heating value.

The DE 197 36 528 and the DE 198 08 533 teach correlative methods where the velocity of sound and the dielectric constant of the combustible gas are measured as the input variables. The gross heating value or the gas composition are calculated from these measurement signals.

The velocity of sound may be measured using an ultrasonic flowmeter. Such meters, which are mainly used in the high-pressure sector, are, however, comparatively expensive. More reasonable ultrasonic flowmeters have been developed for the residential sector. However, these meters have so far failed to successfully compete with the conventional diaphragm meter. Therefore, it is by no means certain that ultrasonic flowmeters will continue to be available for the residential sector in future. The dielectric constant must be determined with a measuring instrument developed especially for this purpose. Therefore, the cost of such measuring equipment is relatively high.

It is necessary to know the properties of a gas, in particular the gross heating value or the Wobbe number, for various industrial applications, in particular for control purposes.

The Wobbe number or the Wobbe index is the quotient of the volume-based gross heating value and the square root of the specific gravity of the gas. The Wobbe index is used in industry to control or maintain the amount of energy supplied to gas consumers. A simple correlative method has yet to be developed for such purposes.

The methane number is an important factor for the operation of gas engines. The methane number is a measure of the knock-resistance of gaseous fuels. The methane number expresses the volume percentage of methane in a methane/hydrogen mixture which, in a test engine under standard conditions, has the same tendency to knock as the fuel gas to be examined. If, for example, a natural gas has a methane number of 85, this means that, under certain engine conditions, this natural gas has the same tendency to knock as a mixture of 85% methane and 15% hydrogen. When the methane number is known, appropriate action can be taken to prevent the undesired knocking of gas-driven piston engines.

DE-A-19650302 teaches a method to determine the methane number. The fuel gas is exposed to infrared radiation. The amount of infrared radiation absorbed by the gas mixture is measured using a radiation detector and the methane number of the fuel gas determined therefrom.

The methane number is determined by means of an optical filter which covers a section of the absorption spectrum in which the hydrocarbons contribute to absorption in a ratio which is virtually proportional to the methane number of the natural gas. The method is relatively simple to use because the components of the infrared sensors can be obtained at a reasonable price and the infrared detectors provide an extremely accurate measurement signal and are easy to use in practice.

With the state-of-the-art methods it has so far not been technically possible to determine the gross heating value of natural gases by means of infrared absorption. The different natural gases may also contain nitrogen in addition to hydrocarbons such as methane, ethane, etc. Depending on the absorption spectrum filtered, the infrared signal reacts very sensitively to volume percentages of hydrocarbons and to volume percentages of carbon dioxide but not to volume percentages of nitrogen. This leads to unacceptable measuring inaccuracies since the volume percentage of nitrogen in the natural gas fluctuates greatly and has a great influence on the gross heating value.

SUMMARY OF THE INVENTION

Thus an object of the present invention is to provide a method for determining the gas properties of a combustible gas, in particular the gross heating value, the Wobbe number and the methane number, which does not involve burning the gas, is simple to use and offers sufficient accuracy for billing and controlling purposes. A further object of the present invention is to create a simple measuring arrangement which can be used under practical conditions.

With the inventive method to determine the gas properties, at least part of the natural gas is exposed to infrared radiation and the amount absorbed by the natural gas is recorded by an infrared sensor for each of two wave lengths or spectral ranges. In addition, the thermal conductivity is measured using a thermal conductivity sensor.

It is important that the three measurands react very differently to the different components and do not correlate.

Thus, the individual components or individual groups of components have each a first degree of influence on the first measurand and a second degree of influence on the second measurand, wherein the first and second wave lengths or spectral ranges are chosen so that the ratio of the first degrees of influence is different to the ratio of the second degrees of influence. E.g. it is possible to determine directly the molar fraction of carbon dioxide in the natural gas using one of the infrared sensors. This sensor operates preferably at a wave length of approx. 4.3 $\mu$m. The second infrared sensor, may detect the hydrocarbons in the natural gas. It preferably operates at a wave length of 3.5 $\mu$m. The wave length was selected so that the sensor is as sensitive as possible to hydrocarbons, namely particularly to ethane, propane and butane. The thermal conductivity is most sensitive to nitrogen. The gas properties are calculated from the signals of the infrared sensors, i.e. the two measured values for the percentage absorbed by the natural gas, and from the signal from the thermal conductivity sensor.

It has proven that the combination of the two signals from the infraered sensors and the signal from the thermal conductivity sonsor provides a very accurate determination of the gas properties for a great variety of natural gas. The inclusion of the signal from the thermal conductivity sensor causes a rapid increase of the accuracy in comparison to a method or apparatus which relies only upon the signals from the infrared sensors.

The advantage of the inventive method is that conventional sensors can be used for the measurements. The sensors are produced in large numbers in series production and are therefore very reasonably priced and reliable. Furthermore, the sensors are very compact so that they can easily be installed in a common housing, for example, a 19" plug-in unit. As the gas passes directly through the sensors and the sensors have a very small volume, the response time is extremely quick, which is very important above all in the control of combustion processes.

The method described hereinabove covers all the different uses of gas property determination described hereinbefore, i.e. energy measurement (gross heating value, normal density, percentage of $CO_2$) and process control (Wobbe number/methane number) at the same time. The accuracy is comparable with the accuracy of the calorimeters or process gas chromatographs previously used for billing. The method described hereinabove is, however, much cheaper and the maintenance costs are much lower.

In principle, different types of sensors can be used to determine the different measurands. However, each type of sensor provides its own type-specific measurement values. Experiments have shown that a simple gas property correlation can be derived from the sensor signals. In particular two empirical relationships are used to establish the correlation. These two empirical relationships were established using laboratory measurements on methane and a number of natural gases. Firstly, the functional relationship between the gross heating value $H_{CH}$ of the hydrocarbons and the quotient of infrared absorption A and the molar fraction $x_{CH}$ of the hydrocarbons was established.

Furthermore, the thermal conductivity $\lambda_{CH}$ of the hydrocarbon gas is described as a function of the quotient of infrared absorption A and the molar fraction $x_{CH}$ of the hydrocarbons. The characteristic curves only have to be established once for a certain sensor type. For any subsequent calibration it is sufficient to randomly check with a pure gas such as methane.

The accuracy of the method can be increased if the amount of infrared radiation absorbed by the combustible gas is determined for an additional wave length of roughly 7.9 $\mu$m. At this wave length, the sensor is particularly sensitive to the volume percentage of methane in the combustible gas. Furthermore, with this additional measurement it is possible to set up a redundant system for testing purposes.

The amount of infrared radiation and the thermal conductivity are preferably recorded under reference conditions in a common measurement environment.

The temperature and the pressure are preferably recorded or kept constant in step a) or b).

The invention is further characterised in that the gas properties are determined according to the formulae (6), (3), (1), (7) (8.1–8.9) and (9) in accordance with FIG. 3.

The formulae (3), (4) and (6) contain the coefficients $a_0$, $a_1$, $a_2$ and $c_0$, $c_1$, $c_2$, which are determined only once from the measurements obtained from the process steps a) and b) on reference gases of known gas composition or gas properties.

Normally three or more reference gases are measured for this purpose. The coefficients are then determined by adjusting to the reference gases by minimising the residual sum of squares by linear regression. The basic calibration is performed only once for a piece of equipment. For recalibration purposes it is sufficient to perform a measurement with only one reference gas, e.g. pure methane (one-point calibration). With this one-point calibration only the coefficients $a_0$ and $c_0$ are adjusted.

The invention also covers a method for determining the amount of energy in a combustible gas, in particular natural gas, characterised in that the gross heating value is determined, the combustible gas is passed through a volume flowmeter and the volume flow rate is measured.

The invention further relates to a device to determine the gas properties of a combustible gas, in particular natural gas, characterised in that the natural gas is passed through an arrangement of sensors which mainly consists of a source of radiation for infrared radiation and at least two radiation detectors assigned to the source of radiation as well as a sensor to record the thermal conductivity, and that the signals of the arrangement of sensors are transmitted to an evaluation unit in which the gas properties are determined by means of a correlation.

The invention is explained in more detail in the following with the aid of a preferred embodiment and the attached drawings.

Figure 5:
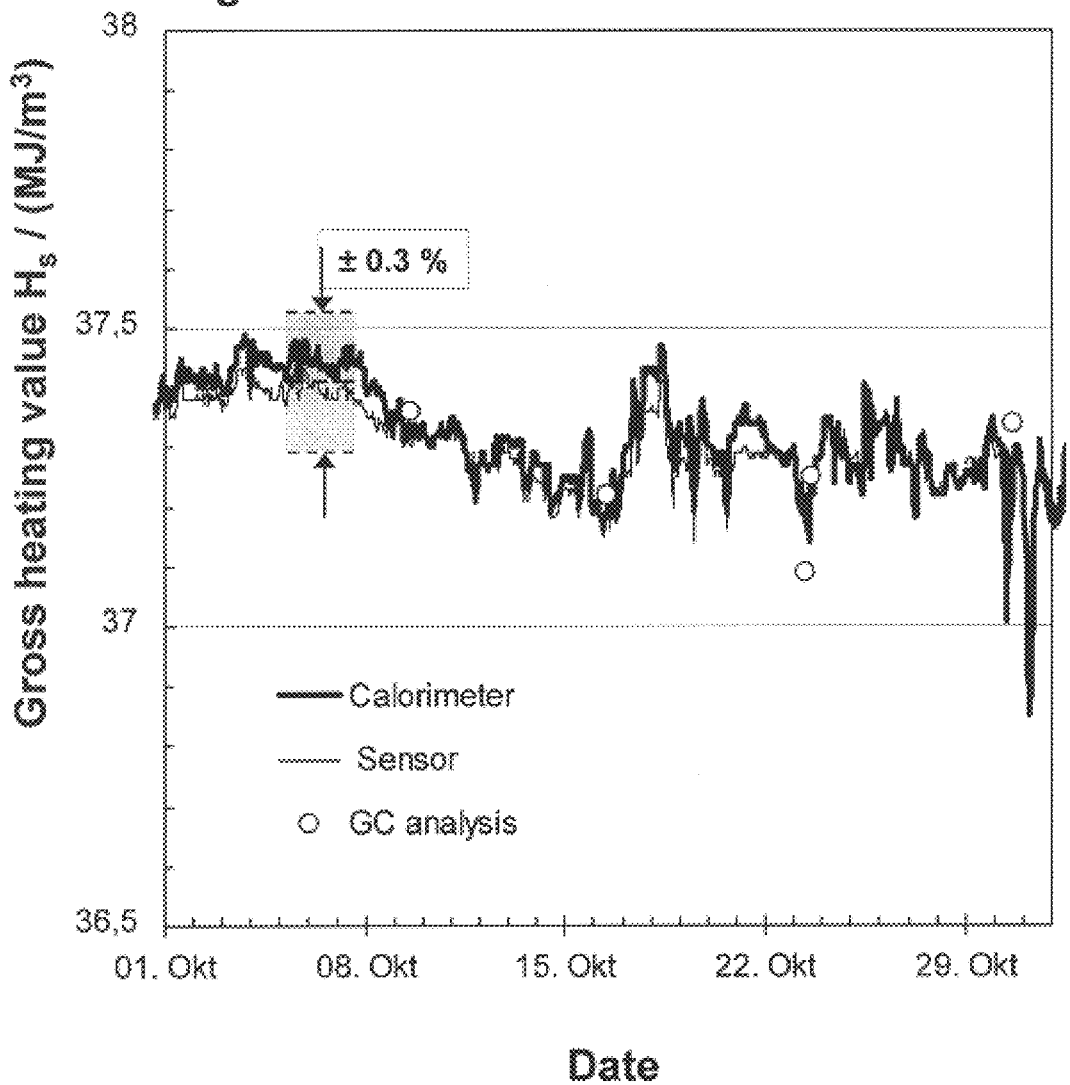

determined according to the inventive procedure with values which have been obtained through gas chromatographic analysis;

FIG. 5: the results of a field test. The gross heating value measured with the inventive device and with a calorimeter over a period of 1 month is shown.

Figure 6:
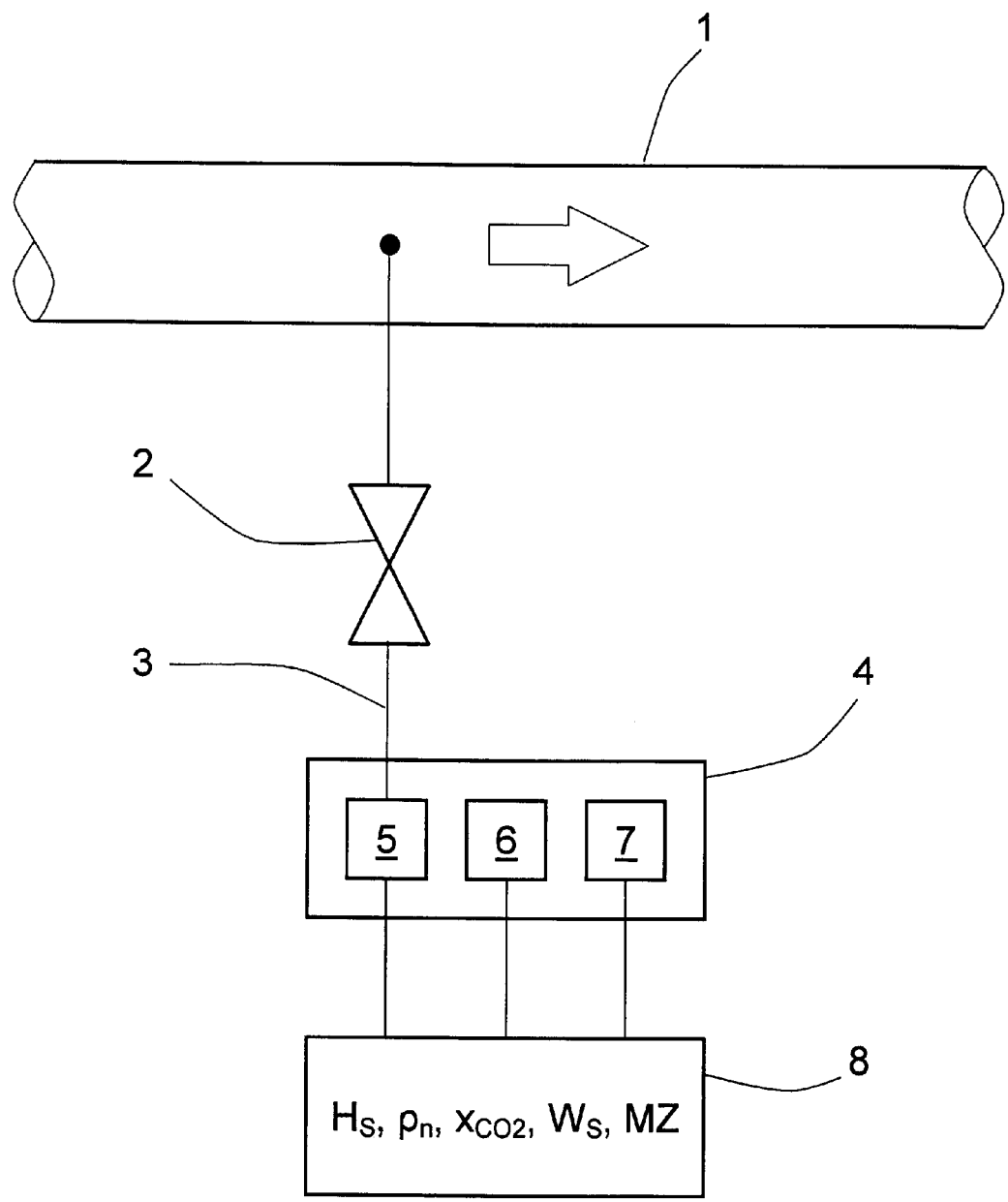

FIG. 6 a schematic of the arrangement of measuring instruments to determine the gas properties of natural gases.

DETAILED DESCRIPTION OF THE INVENTION

Figure 3:
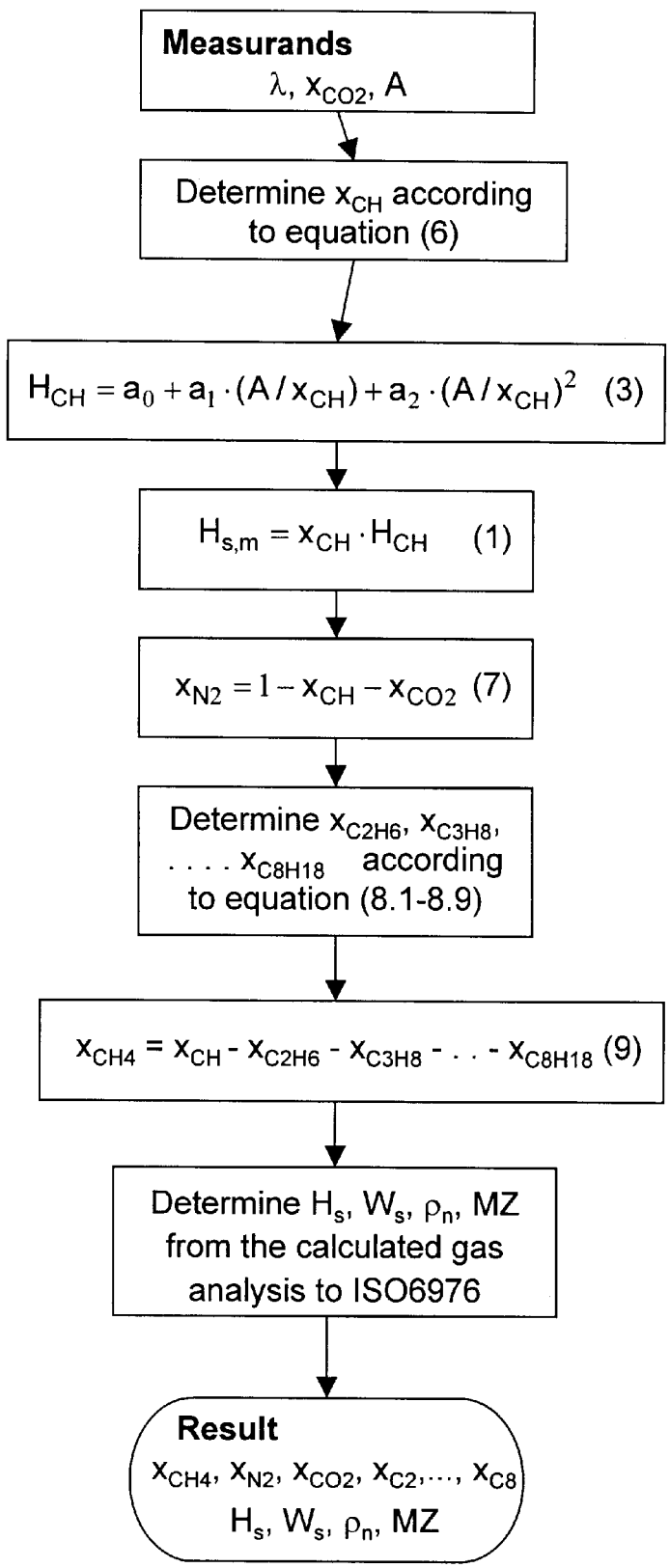
FIG. 3: a calculation procedure to determine the gas composition and the gas properties (gross heating value, Wobbe number, normal density, methane number) from the thermal conductivity $\lambda$, molar fraction of carbon dioxide $x_{CO2}$, which results directly from the measurement of infrared absorption at a wave length of approx. 4.3 $\mu$m and infrared absorption of the hydrocarbons A.

The following describes the calculation procedure and the correlation method according to FIG. 3.

The thermal conductivity $\lambda$, the molar fraction of carbon dioxide $x_{CO2}$ which results directly from the measurement of infrared absorption at a wave length of approx. 4,3 $\mu$m and the infrared absorption of hydrocarbons A are measured as input variables.

Natural gas consists substantially of nitrogen, carbon dioxide as well as a hydrocarbon gas, hereinafter referred to as CH, which is mainly composed of the alkanes methane to octane. As the amount of nitrogen and the amount of carbon dioxide have no influence on the gross heating value, the molar gross heating value $H_{s,m}$ of the natural gas results from the molar fraction $x_{CH}$, the gross heating value $H_{CH}$ ($H_{CH}=\Sigma x_{CHi} \cdot H_{CHi}$) of the hydrocarbon gas:

$$H_{s,m}=x_{CH} \cdot H_{CH} \tag{1}$$

The molar fraction of the hydrocarbon gas is as follows:

$$x_{CH}=1-x_{N2}-x_{CO2} \tag{2}$$

Figure 1:
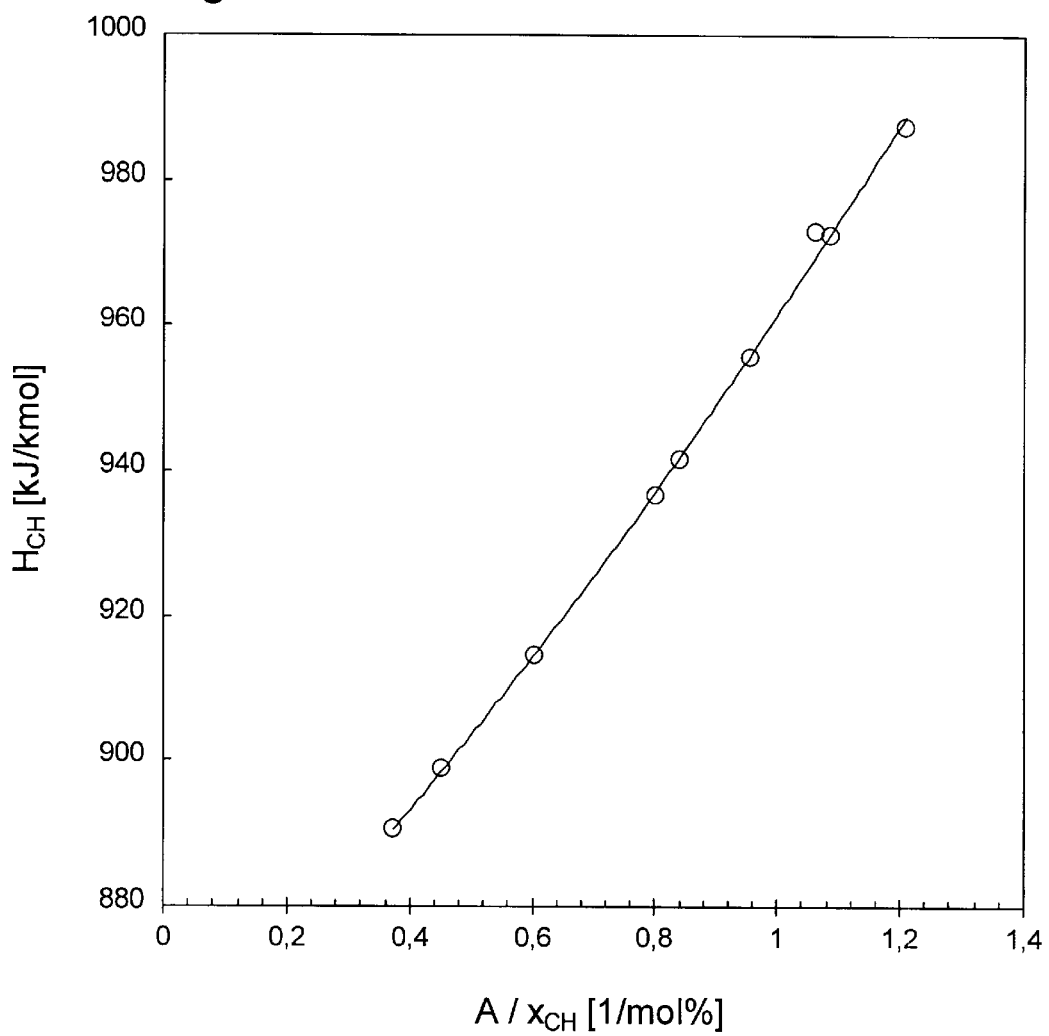
FIG. 1: the molar gross heating value $H_{CH}$ of the hydrocarbon gas as a function of the quotient of infrared absorption A and the molar fraction $x_{CH}$ of the hydrocarbons for 8 natural gases as well as methane.

As shown in FIG. 1, the gross heating value of the hydrocarbon gas $H_{CH}$ can be shown as a function of the quotient of infrared absorption of the hydrocarbons A and the molar fraction of the hydrocarbons $x_{CH}$:

$$H_{CH}=a_0+a_1 \cdot (A/x_{CH})+a_2 \cdot (A/x_{CH})^2 \tag{3}$$

This can be explained by the fact that the molar fractions of the alkanes are distributed regularly in the natural gas. The infrared absorption A in equation (3) is measured with the infrared sensor at a wave length of 3,5 $\mu$m.

Figure 2:
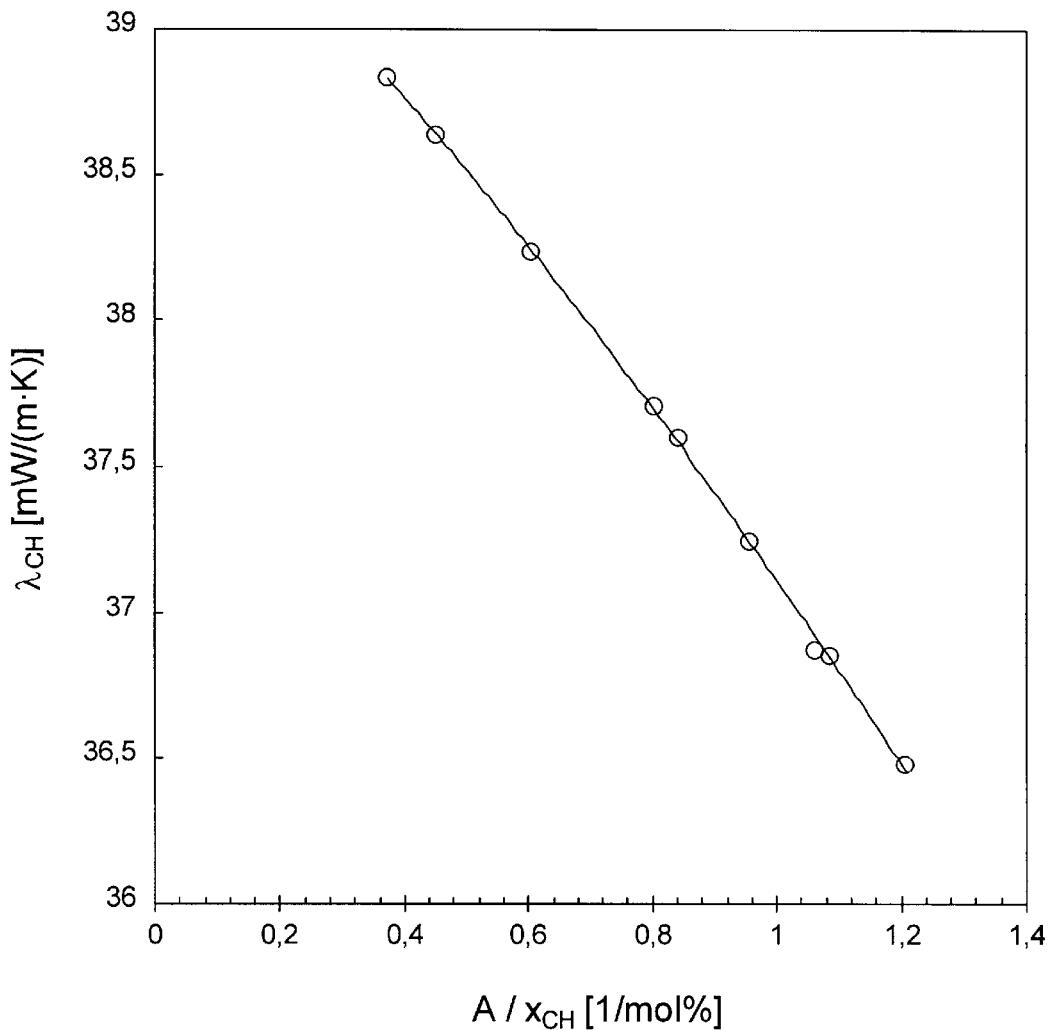
FIG. 2: the thermal conductivity $\lambda_{CH}$ of the hydrocarbon gas as a function of the quotient of infrared absorption A and the molar fraction $x_{CH}$ of the hydrocarbons for 8 natural gases as well as methane.

The thermal conductivity $\lambda_{CH}$ of the hydrocarbon gas can also be shown in a similar manner as a function of the quotient $(A/x_{CH})$. This relationship is shown in FIG. 2.

$$\lambda_{CH}=c_0+c_1 \cdot (A/x_{CH})+c_2 \cdot (A/x_{CH})^2 \tag{4}$$

The thermal conductivity $\lambda$ of the natural gas can be shown as a function of the molar fractions $x_{N2}$, $x_{CO2}$ and $x_{CH}$ as follows:

$$\lambda=x_{N2} \cdot \lambda_{N2}+x_{CO2} \cdot \lambda_{CO2}+x_{CH} \cdot \lambda_{CH} \tag{5}$$

The molar fraction of the hydrocarbon gas $x_{CH}$ can be directly derived from the measurands $x_{CO2}$, A and $\lambda$ by inserting equation (4) in equation (5) and solving for $x_{CH}$:

$$x_{CH} = \sqrt{\frac{1}{4}\left[\frac{c_1 \cdot A - \lambda + x_{CO2}(\lambda_{CO2} - \lambda_{N2}) + \lambda_{N2}}{c_0 - \lambda_{N2}}\right]^2 - \frac{c_2 \cdot A^2}{(c_0 - \lambda_{N2})}} - \frac{1}{2} \cdot \frac{c_1 \cdot A - \lambda + x_{CO2}(\lambda_{CO2} - \lambda_{N2}) + \lambda_{N2}}{c_0 - \lambda_{N2}} \tag{6}$$

Values for the thermal conductivity of the pure substances $\lambda_{N2}$ and $\lambda_{CO2}$ can be found in literature.

The gross heating value $H_{CH}$ of the hydrocarbon gas can be calculated from the molar fraction of the hydrocarbon gas using equation (3) and then the gross heating value of the natural gas from equation (1).

The molar fraction of the nitrogen $x_{N2}$ can then be determined as follows from the molar fractions $x_{CH}$ and $x_{CO2}$.

$$x_{N2}=1-x_{CO2} \tag{7}$$

The relative densities of the individual alkanes from ethane to octane can be derived from the gross heating value $H_{CH}$ and the molar fractions $x_{CH}$ of the hydrocarbon gas as follows:

$$x_{C2H6}=\{\alpha_1(H_{CH}-H_{CH4})+\beta_1(H_{CH}-H_{CH4})^2\} \tag{8.1}$$

$$x_{C3H8}=\{\alpha_2(H_{CH}-H_{CH4})+\beta_2(H_{CH}-H_{CH4})^2\} \tag{8.2}$$

$$x_{n-C4H10}=\{\alpha_3(H_{CH}-H_{CH4})+\beta_3(H_{CH}-H_{CH4})^2\} \tag{8.3}$$

$$x_{i-C4H10}=\{\alpha_4(H_{CH}-H_{CH4})+\beta_4(H_{CH}-H_{CH4})^2\} \tag{8.4}$$

$$x_{n-C5H12}=\{\alpha_5(H_{CH}-H_{CH4})+\beta_5(H_{CH}-H_{CH4})^2\} \tag{8.5}$$

$$x_{i-C5H12}=\{\alpha_6(H_{CH}-H_{CH4})+\beta_6(H_{CH}-H_{CH4})^2\} \tag{8.6}$$

$$x_{n-C6H14}=\{\alpha_7(H_{CH}-H_{CH4})+\beta_7(H_{CH}-H_{CH4})^2\} \tag{8.7}$$

$$x_{n-C7H16}=\{\alpha_8(H_{CH}-H_{CH4})+\beta_8(H_{CH}-H_{CH4})^2\} \tag{8.8}$$

$$x_{n-C8H18}=\{\alpha_9(H_{CH}-H_{CH4})+\beta_9(H_{CH}-H_{CH4})^2\} \tag{8.9}$$

The coefficients $\alpha_1$ to $\beta_9$ are determined only once using the analysis of several reference gases with a known gas composition or gas properties. The coefficients are determined by adjusting to the reference gases by minimising the residual sum of squares by linear regression.

The molar fraction of the methane is then as follows:

$$x_{CH4}=x_{CH}-x_{C2H6}-x_{C3H8}-x_{n-C4H10}-x_{i-C4H10}-x_{n-C5H12}-x_{n-C6H14}-x_{n-C7H16}-x_{n-C8H18} \tag{9}$$

The gas analysis of a total of 12 components ($N_2$, $CO_2$, 10 alkanes) thus determined can now be used to derive further gas properties such as the volumetric gross heating value $H_s$, the Wobbe number $W_s$, the normal density $\rho_n$ or the methane number MN. $H_s$, $W_s$ and $\rho_n$ are calculated according to the international standard ISO6976. A schematic of the calculation procedure is shown in FIG. 3.

The calculation procedure described contains the coefficients $a_0$, $a_1$, $a_2$ and $c_0$, $c_1$, $c_2$, which are determined by a single basic calibration. Calibration is performed by measurements (process steps a) and b)) on reference gases whose gas composition or gas properties are known. Normally three or more reference gases are measured for this purpose. The coefficients are determined by adjusting to the reference gases by minimising the residual sum of squares by linear regression. This basic calibration is performed only once for a piece of equipment. It is sufficient for any subsequent recalibration to perform a measurement with only one reference gas, e.g. pure methane (one-point calibration). With this one-point calibration, only the coefficients $a_0$ and $c_0$ are then adjusted.

Figure 4:
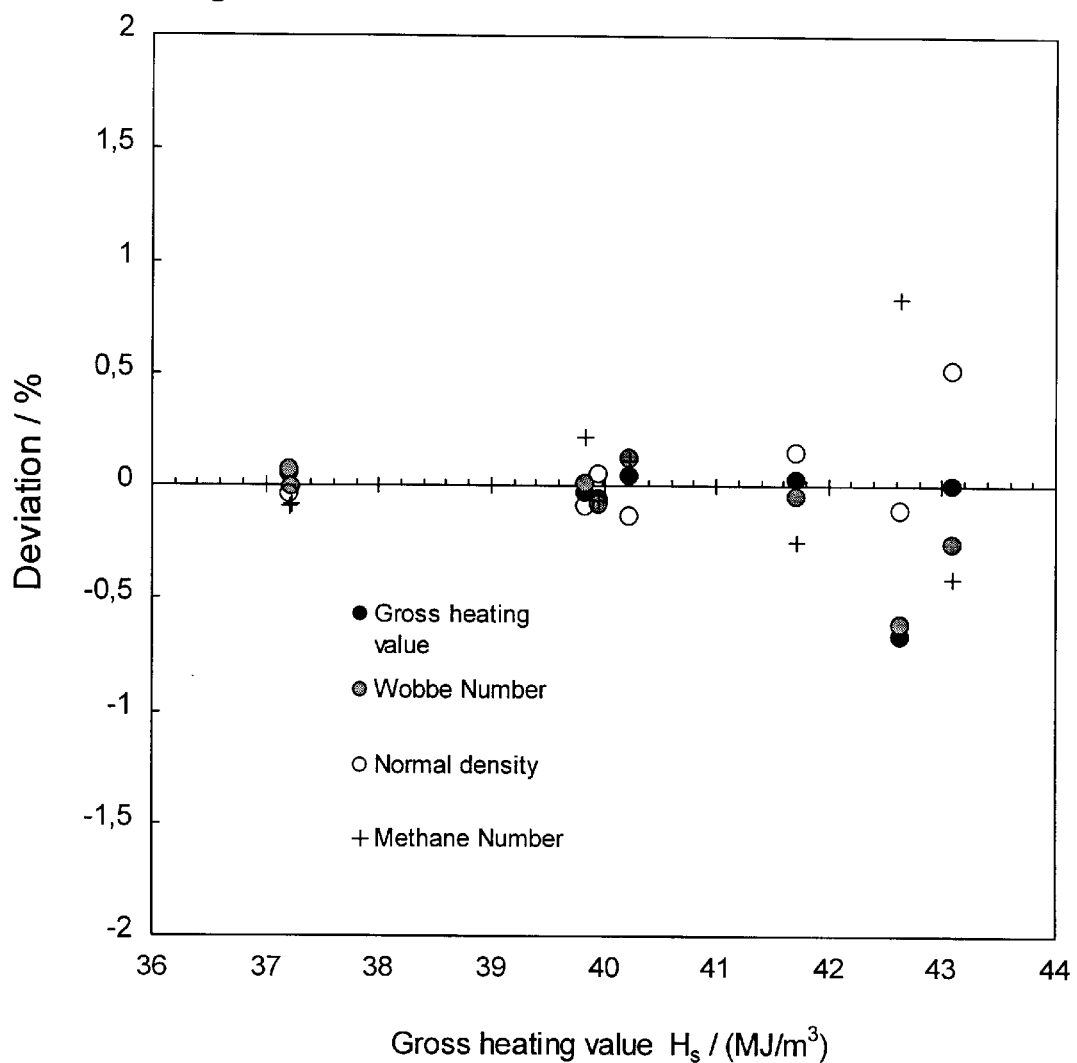
FIG. 4: a comparison of gas properties (gross heating value, Wobbe number, normal density, methane number)

The method was tested in the laboratory on a total of 8 different natural gases. FIG. 4 shows the procentual deviations of the gas properties (gross heating value, Wobbe number, normal density and methane number) measured with the arrangement of sensors and the values derived from gas chromatographic analysis. Generally, the deviations for the gross heating value are less ±0.2%. Only with one gas sample was the deviation 0.6%.

The long-term stability was examined in a field test where the measurement signals were continually recorded and compared with a calorimeter which is used for billing purposes. The result is shown in FIG. 5 for a period of 1 month. The figure shows that the correlation of the gross heating value derived from the arrangement of sensors and the gross heating value measured with the calorimeter is better than 0.2%. Therefore, both methods correspond within the uncertainty of measurement of the calorimeter (0.3%). No significant drift of the measurement signal was observed during the entire field test which was carried over a period of four months.

FIG. 6 shows a schematic of the inventive device. Part of a stream of natural gas is withdrawn from a main transmission line 1 and passed through a pressure-reducing device 2 into a branch line 3 at approx. 20–100 mbar, i.e. substantially reduced to atmospheric pressure, and then passed into an arrangement of sensors 4. The arrangement of sensors 4 consists substantially of a source of infrared radiation, which is not shown, and two radiation detectors 5, 6 assigned to the source of radiation. A third sensor 7 measures the thermal conductivity. The sensors 5, 6, 7 continually record the measurement signals which are directly evaluated by an electronic evaluation unit 8 (conventional printed circuit).

The temperature is measured in a manner not shown so that it is possible to convert the measured values to reference conditions. If the temperature fluctuates sharply in the measurement environment, it is advantageous to set or adjust the temperature to a figure of for example 50° C.

What is claimed is:

1. A method of determining the properties of a combustible gas, in particular of natural gas, said combustible gas consisting of a plurality of different components or different groups of components and having a thermal conductivity, said method comprising the following steps:
    a) at least a part of the combustible gas is exposed to infrared radiation and the amount of infrared radiation absorbed by the combustible gas is recorded at least for a first wave length or spectral range and a second wave length or spectral range, thus providing a first and a second measurand, wherein the first and second wave lengths or spectral ranges are different,
    b) the thermal conductivity of the combustible gas is recorded, thus providing a third measurand and
    c) the gas properties of the combustible gas are determined from the at least three measurands.
2. The method according to claim 1,
    wherein the combustible gas contains hydrocarbons and carbon dioxide and wherein the first and second wave lengths or spectral ranges are chosen so that the amount of hydrocarbons is detected from the first measurand and the amount of carbon dioxide is detected from the second measurand.
3. The method according to claim 2,
    wherein the amount of infrared radiation absorbed by the combustible gas is recorded for the wave lengths of approximately 3.5 $\mu$m and 4.3 $\mu$m.
4. The method according to claim 2,
    wherein the combustible gas contains methane and wherein the amount of infrared radiation absorbed by the combustible gas is also recorded for a third wave length or spectral range thus providing a fourth measurand for determining the properties of the combustible gas.
5. The method according to claim 3,
    wherein the third wave length is approximately 7.9 $\mu$m.
6. The method according to claim 1,
    wherein the amount of infrared radiation absorbed by the combustible gas as well as the thermal conductivity are recorded under reference conditions in a common measuring environment.
7. The method according to claim 1,
    wherein the temperature and the pressure are recorded in step a) or b).
8. The method according to claim 1,
    wherein the temperature and the pressure are kept constant in step a) or b).
9. A device for determining the gas properties of a combustible gas, in particular of natural gas,
    wherein the combustible gas is fed into an arrangement of sensors (4) which comprises a source of infrared radiation and at least two radiation detectors (5, 6) assigned to the source of radiation as well as a sensor (7) to record the thermal conductivity and wherein the signals of the arrangement of sensors are transmitted to an evaluation device in which the gas properties are determined by means of a correlation.
10. The device according to claim 9,
    wherein an optical filter is assigned to each of the radiation detectors (5,6),
    wherein the optical filters are chosen such that the amount of hydrocarbons and the amount of carbon dioxide is detected.

* * * * *

UNITED STATES PATENT AND TRADEMARK OFFICE
CERTIFICATE OF CORRECTION

PATENT NO. : 6,490,908 B2
DATED : December 10, 2002
INVENTOR(S) : Schley

It is certified that error appears in the above-identified patent and that said Letters Patent is hereby corrected as shown below:

<u>Title page,</u>
Item [73], Assignee, please delete "Buhrgas Aktiengesellschaft" and insert
-- Ruhrgas Aktiengesellschaft --.

Signed and Sealed this

Thirtieth Day of September, 2003

JAMES E. ROGAN
*Director of the United States Patent and Trademark Office*